(12) United States Patent
Jouhanneaud

(10) Patent No.: US 10,753,937 B2
(45) Date of Patent: *Aug. 25, 2020

(54) IGF-1R ANTIBODY AND ITS USE FOR THE DIAGNOSIS OF CANCER

(71) Applicant: PIERRE FABRE MEDICAMENT, Boulogne-billancourt (FR)

(72) Inventor: Alexandra Jouhanneaud, Bonneville (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/569,566

(22) PCT Filed: Apr. 27, 2016

(86) PCT No.: PCT/EP2016/059338
§ 371 (c)(1),
(2) Date: Oct. 26, 2017

(87) PCT Pub. No.: WO2016/174053
PCT Pub. Date: Nov. 3, 2016

(65) Prior Publication Data
US 2019/0049457 A1  Feb. 14, 2019

(30) Foreign Application Priority Data

Apr. 27, 2015  (EP) .................... 15305642

(51) Int. Cl.
*C07K 16/28* (2006.01)
*A61K 47/68* (2017.01)
*G01N 33/574* (2006.01)

(52) U.S. Cl.
CPC ... *G01N 33/57492* (2013.01); *A61K 47/6803* (2017.08); *A61K 47/6849* (2017.08); *C07K 16/2863* (2013.01); *C07K 2317/77* (2013.01); *C07K 2317/92* (2013.01); *G01N 2333/4745* (2013.01); *G01N 2333/65* (2013.01); *G01N 2800/52* (2013.01)

(58) Field of Classification Search
None
See application file for complete search history.

(56) References Cited

U.S. PATENT DOCUMENTS

2011/0287451 A1* 11/2011 Klinguer-Hamour ..................... C07K 16/2866
435/7.23

OTHER PUBLICATIONS

International Search Report dated Jun. 29, 2016, in corresponding PCT International Application.
European Search Report dated Oct. 6, 2015, in corresponding European Application.
Marie-Paule Lefranc; "Unique Database Numbering System for Immunogenetic Analysis", Immunology Today, vol. 18, No. 11, 1 page (1997).
Marie-Paule Lefranc; "The IMGT Unique Numbering for Immunoglobulins, T-Cell Receptors, and Ig-Like Domains", The Immunologist, vol. 7, No. 4, pp. 132-136 (1999).
Marie-Paule Lefranc et al.; "IMGT Unique Numbering for Immunoglobulin and T Cell Receptor Variable Domains and Ig Superfamily V-Like Domains", Developmental and Comparative Immunology, vol. 27, pp. 55-77 (2003).
Manuel Ruiz et al.; "IMGT Gene Identification and Colliers de Perles of Human Immunoglobulins with known 3D Structures", Immunogenetics, vol. 53, pp. 857-883 (2002).
Quentin Kaas et al.; "IMGT Colliers de Perles: Standardized Sequence-Structure Representations of the IgSF and MhcSF Superfamily Domains", Current Bioinformatics, vol. 21-30 (2007).
Quentin Kaas et al.; "IMGT/3Dstructuer-DB and IMGT/StructuralQuery, a Database and a Tool for Immunoglobulin, T Cell Receptor and MHC Structural Data", Nucleic Acids Research, vol. 32, Database Issue, pp. D208-D210 (2004).
Saul B. Needleman et al.; "A General Method Applicable to the Search for Similarities in the Amino Acid Sequence of Two Proteins", J. Mol. Biol., vol. 48, pp. 443-453 (1970).
William R. Pearson et al.; "Improved Tools for Biological Sequence Comparison", Proc. Natl. Acad. Sci. USA, vol. 85, pp. 2444-2448 (1988).
Jean F. Simpson et al.; "Prognostic Value of Histologic Grade and Proliferative Activity in Axillary Node-Positive Breast Cancer: Results from the Eastern Cooperative Oncology Group Companion Study, EST 4189", Journal of Clinical Oncology, vol. 18, No. 10, pp. 2059-2069 (2000).
S.J.L. Payne et al.; "Predictive Markers in Breast Cancer—The Present", Histopathology, vol. 52, pp. 82-90 (2007).
Jennet M. Harvey et al.; "Estrogen Receptor Status by Immunohistochemistry is Superior to the Ligand-Binding Assay for Predicting Response to Adjuvant Endocrine Therapy in Breast Cancer", Journal of Clinical Oncology, vol. 17, No. 5, pp. 1474-1481 (1999).

* cited by examiner

*Primary Examiner* — Marianne P Allen
(74) *Attorney, Agent, or Firm* — Finnegan, Henderson, Farabow, Garrett & Dunner, L.L.P.

(57) ABSTRACT

The present disclosure relates to IGF-IR (insulin like growth factor receptor-1) antibodies characterized by CDR sequences a, to be used in detection methods of IGF-IR expressing tumoral cells.

Figure 1:
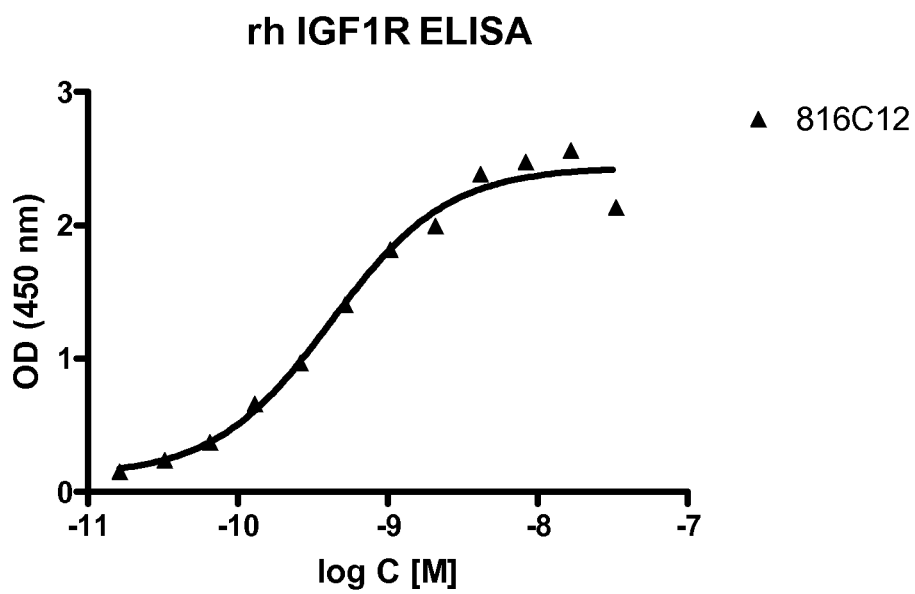

5 Claims, 5 Drawing Sheets
Specification includes a Sequence Listing.

|  | 816C12 |
|---|---|
| Sigmoidal dose-response (variable slope) Best-fit values | |
| BOTTOM | 0.1163 |
| TOP | 2.438 |
| LOGEC50 | -9.380 |
| HILLSLOPE | 1.116 |
| EC50 | 4.173e-010 |

SEQUENCE LISTING

<160> NUMBER OF SEQ ID NOS: 10

<210> SEQ ID NO 1
<211> LENGTH: 8
<212> TYPE: PRT
<213> ORGANISM: artificial
<220> FEATURE:
<223> OTHER INFORMATION: 816C12 I-4894, heavy chain, CDR-H1

<400> SEQUENCE: 1

Gly His Thr Phe Thr Ser Tyr Val
1               5

<210> SEQ ID NO 2
<211> LENGTH: 8
<212> TYPE: PRT
<213> ORGANISM: artificial
<220> FEATURE:
<223> OTHER INFORMATION: 816C12 I-4894, heavy chain, CDR-H2

<400> SEQUENCE: 2

Ile Asn Pro His Asn Asp Val Thr
1               5

<210> SEQ ID NO 3
<211> LENGTH: 14
<212> TYPE: PRT
<213> ORGANISM: artificial
<220> FEATURE:
<223> OTHER INFORMATION: 816C12 I-4894, heavy chain, CDR-H3

<400> SEQUENCE: 3

Val Ser Thr Ala Tyr Tyr Gly Asn Gly Arg Tyr Phe Asp Val
1               5                   10

<210> SEQ ID NO 4
<211> LENGTH: 6
<212> TYPE: PRT
<213> ORGANISM: artificial
<220> FEATURE:
<223> OTHER INFORMATION: 816C12 I-4894, light chain, CDR-L1

<400> SEQUENCE: 4

Gln Asp Ile Asn Asn Tyr
1               5

<210> SEQ ID NO 5
<211> LENGTH: 3
<212> TYPE: PRT
<213> ORGANISM: artificial
<220> FEATURE:
<223> OTHER INFORMATION: 816C12 I-4894, light chain, CDR-L2

<400> SEQUENCE: 5

Tyr Thr Ser
1

<210> SEQ ID NO 6
<211> LENGTH: 9
<212> TYPE: PRT
<213> ORGANISM: artificial
<220> FEATURE:
<223> OTHER INFORMATION: 816C12 I-4894, light chain, CDR-L3

<400> SEQUENCE: 6

Gln Gln Gly Asn Thr Leu Pro Trp Thr
1               5

<210> SEQ ID NO 7
<211> LENGTH: 121
<212> TYPE: PRT
<213> ORGANISM: artificial
<220> FEATURE:
<223> OTHER INFORMATION: 816C12 I-4894, heavy chain, Variable domain

<400> SEQUENCE: 7

Glu Val Gln Leu Gln Gln Ser Gly Pro Glu Leu Val Lys Pro Gly Ala
1               5                   10                  15

Ser Val Lys Met Ser Cys Lys Ala Ser Gly His Thr Phe Thr Ser Tyr
            20                  25                  30

Val Leu His Trp Met Lys Arg Lys Pro Gly Gln Gly Leu Glu Trp Ile
        35                  40                  45

Gly Tyr Ile Asn Pro His Asn Asp Val Thr Lys Tyr Asn Glu Asn Phe
    50                  55                  60

Lys Gly Lys Ala Thr Leu Thr Ser Asp Lys Tyr Ser Ser Thr Val Tyr
65                  70                  75                  80

Met Glu Val Ser Ser Leu Thr Ser Glu Asp Ser Ala Val Tyr Tyr Cys
                85                  90                  95

Val Ser Thr Ala Tyr Tyr Gly Asn Gly Arg Tyr Phe Asp Val Trp Gly
            100                 105                 110

Ala Gly Thr Thr Val Thr Val Ser Ser
        115                 120

<210> SEQ ID NO 8
<211> LENGTH: 107
<212> TYPE: PRT
<213> ORGANISM: artificial
<220> FEATURE:
<223> OTHER INFORMATION: 816C12 I-4894, light chain, Variable domain

<400> SEQUENCE: 8

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Ser Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 9
<211> LENGTH: 363
<212> TYPE: DNA
<213> ORGANISM: artificial
<220> FEATURE:
<223> OTHER INFORMATION: 816C12 I-4894, heavy chain, Variable domain

<400> SEQUENCE: 9
gaggtccagc tgcagcagtc tggacctgag ctggtaaagc ctggggcttc agtgaagatg        60
tcctgcaagg cttctggaca cacattcact agctatgttt tgcactggat gaagcggaag       120

```
cctgggcagg gccttgagtg gattggatat attaatcctc acaatgatgt tactaagtac      180
aatgagaatt tcaaaggcaa ggccacactg acttcagaca aatactccag cacagtctac      240
atggaggtca gcagcctgac ctctgaggac tctgcggtgt attactgtgt aagtaccgcc      300
tactatggta acggccggta cttcgatgtc tggggcgcag ggaccacggt caccgtctcc      360
tca                                                                   363

<210> SEQ ID NO 10
<211> LENGTH: 321
<212> TYPE: DNA
<213> ORGANISM: artificial
<220> FEATURE:
<223> OTHER INFORMATION: 816C12 I-4894, light chain, Variable domain

<400> SEQUENCE: 10
gatatccaga tgacacagac tacatcctcc ctgtctgcct ctctgggaga cagagtcacc       60
atcagttgca gggcaagtca ggacattaac aattatttaa actggtatca gcagaaacca      120
gatggaactg ttaaactcct gatctactac acatcaagat tacactcagg agtctcatca      180
aggttcagtg gcagtgggtc tggaacagat tattctctca ccattagcaa cctggagcaa      240
gaagatattg ccacttattt ttgccaacag ggtaatacgc ttccgtggac gttcggtgga      300
ggcaccaagc tggaaatcaa a                                                321
```

IGF-1R ANTIBODY AND ITS USE FOR THE DIAGNOSIS OF CANCER

The present invention relates to a novel antibody, in particular a monoclonal antibody, capable of binding to IGF-1R, as well as the amino and nucleic acid sequences coding for said antibody.

The insulin-like growth factor 1 receptor called IGF-1R (or sometimes IGF1R) is a receptor with tyrosine kinase activity having 70% homology with the insulin receptor IR. IGF-1R is a glycoprotein of molecular weight approximately 350,000. It is a hetero-tetrameric receptor of which each half-linked by disulfide bridges—is composed of an extracellular α-subunit and of a transmembrane β-subunit. IGF-1R binds IGF1 and IGF2 with a very high affinity (Kd #1 nM) but is equally capable of binding to insulin with an affinity 100 to 1000 times lower. Conversely, the IR binds insulin with a very high affinity although the IGFs only bind to the insulin receptor with a 100 times lower affinity. The tyrosine kinase domains of IGF-1R and of IR have a very high sequence homology although the zones of weaker homology respectively concern the cysteine-rich region situated on the α-subunit and the C-terminal part of the β-subunit. The sequence differences observed in the α-subunit are situated in the binding zone of the ligands and are therefore at the origin of the relative affinities of IGF-1R and of IR for the IGFs and insulin respectively. The differences in the C-terminal part of the β-subunit result in a divergence in the signalling pathways of the two receptors; IGF-1R mediating mitogenic, differentiation and antiapoptosis effects, while the activation of the IR principally involves effects at the level of the metabolic pathways.

The role of the IGF system in carcinogenesis has become the subject of intensive research in the last 20 years. This interest followed the discovery of the fact that in addition to its mitogenic and antiapoptosis properties. IGF-1R seems to be required for the establishment and the maintenance of a transformed phenotype. In fact, it has been well established that an overexpression or a constitutive activation of IGF-1R leads, in a great variety of cells, to a growth of the cells independent of the support in media devoid of foetal calf serum, and to the formation of tumors in nude mice. This in itself is not a unique property since a great variety of products of overexpressed genes can transform cells, including a good number of receptors of growth factors. However, the crucial discovery which has clearly demonstrated the major role played by IGF-1R in the transformation has been the demonstration that the IGF-1R-cells, in which the gene coding for IGF-1R has been inactivated, are totally refractory to transformation by different agents which are usually capable of transforming the cells, such as the E5 protein of bovine papilloma virus, an overexpression of EGFR or of PDGFR, the T antigen of SV 40, activated Ras or the combination of these two last factors.

In such a context IGF-1R has been considered for a long time as an interesting target in oncology. A large number of projects targeting IGF-1R (humanized or human antibodies or small molecules) have been initiated to develop IGF-1R antagonists for the treatment of cancers and more than 70 clinical trials have been performed in various indications. Nevertheless, at this date, none of these projects have been successful and there are no IGF-1R antibodies on the market.

The present invention aims to provide at least one reagent that can be used as a diagnostic or prognosis biomarker for detecting and/or monitoring oncogenic disorders especially those characterized by expression of IGF-1R or those that are mediated by aberrant IGF-1R expression.

Previous attempts to develop a valuable antibody that can be used as a relevant diagnostic or prognostic tool have been reported but none of these are giving satisfaction.

As it will be apparent from the following examples, the inventors have been surprised to demonstrate that the commercial antibodies commonly used at this day for the scoring of the IGF-1R expressing tumors seem to be not relevant as they give false positive and/or false negative. This issue has lead, in part, to the failure of clinical trials with IGF-1R antibodies due to the selection of the patients rather than the real activity of the IGF-1R antibodies.

Moreover, first studies performed using commercial antibodies showed discrepancy between IGF-1R scoring and anti-tumoral activity of targeted ADC therapy.

The present invention intends to remedy this issue by providing a novel antibody which, contrary to the existing ones, is capable of straining which do correlate with the pharmacology of IGF-1R targeted therapy.

In a first aspect, a subject of the invention is an isolated antibody, or an antigen-binding fragment thereof, that binds to the IGF-1R, preferably human IGF-1R, with high affinity and can thus be useful in methods to diagnose pathological hyperproliferative oncogenic disorders mediated by IGF-1R expression.

An embodiment of the invention relates to an antibody, or an antigen-binding fragment thereof, comprising the six CDRs of sequences SEQ ID Nos. 1, 2, 3, 4, 5 and 6.

In a particular embodiment, the invention relates to an IGF-1R antibody, or an antigen-binding fragment thereof, characterized in that it comprises:

i) a heavy chain with CDR-H1 of sequence SEQ ID No. 1, CDR-H2 of sequence SEQ ID No. 2 and CDR-H3 of sequence SEQ ID No. 3; and ii) a light chain with CDR-L1 of sequence SEQ ID No. 4, CDR-L2 of sequence SEQ ID No. 5 and CDR-L3 of sequence SEQ ID No. 6.

The terms "antibody", "antibodies" "ab" or "immunoglobulin" are used interchangeably in the broadest sense and include monoclonal antibodies, isolated, engineered, chemically synthesized, or recombinant antibodies (e.g., full length or intact monoclonal antibodies), polyclonal antibodies, multivalent antibodies or multispecific antibodies (e.g., bispecific antibodies) and also antibody fragment, so long as they exhibit the desired biological activity. In an embodiment, the invention relates to a recombinant antibody.

As used in the present specification, the expression "IGF-1R antibody" should be interpreted as similar to "anti-IGF-1R antibody" and means an antibody capable of binding to IGF-1R.

By "IGF-1R binding fragment" or "antigen-binding fragment" of an antibody, it is intended to indicate any peptide, polypeptide, or protein retaining the ability to bind to the IGF-1R target (also generally referred as antigen) of the antibody. In an embodiment, such "antigen binding fragments" are selected in the group consisting of Fv, scFv (sc for single chain), Fab, F(ab')$_2$, Fab', scFv-Fc fragments or diabodies, or any fragment of which the half-life time would have been increased by chemical modification, such as the addition of poly(alkylene) glycol such as poly(ethylene) glycol ("PEGylation") (pegylated fragments called Fv-PEG, scFv-PEG, Fab-PEG, F(ab')$_2$-PEG or Fab'-PEG) ("PEG" for Poly(Ethylene) Glycol), or by incorporation into a liposome, said fragments having at least one of the characteristic CDRs of the antibody according to the invention. Preferably, said "antigen binding fragments" will be constituted or will comprise a partial sequence of the heavy or light variable chain of the antibody from which they are derived, said partial sequence being sufficient to retain the same specificity of binding as the antibody from which it is descended and a sufficient affinity, preferably at least equal to 1/100, in a more preferred manner to at least 1/10, of the affinity of the antibody from which it is descended, with respect to the target.

Preferably, said "IGF-1R binding fragment" or "antigen-binding fragment" comprises at least:

i) the CDR-H1 of sequence SEQ ID No. 1, CDR-H2 of sequence SEQ ID No. 2 and CDR-H3 of sequence SEQ ID No. 3; and ii) the CDR-L1 of sequence SEQ ID No. 4, CDR-L2 of sequence SEQ ID No. 5 and CDR-L3 of sequence SEQ ID No. 6.

By "binding", "binds", or the like, it is intended that the antibody, or any antigen-binding fragment thereof, forms a complex with an antigen that is relatively stable under physiologic conditions. Specific binding can be characterized by an equilibrium dissociation constant of at least about $1 \times 10^{-6}$ M or less. Methods for determining whether two molecules bind are well known in the art and include, for example, equilibrium dialysis, surface plasmon resonance, and the like. For the avoidance of doubt, it does not mean that the said antibody could not bind or interfere, at a low level, to another antigen. Nevertheless, as an embodiment, the said antibody binds only to the said antigen.

By CDR regions or CDR(s), it is intended to indicate the hypervariable regions of the heavy and light chains of the immunoglobulins as defined by IMGT.

The IMGT unique numbering has been defined to compare the variable domains whatever the antigen receptor, the chain type, or the species [Lefranc M.-P., Immunology Today 18, 509 (1997)/Lefranc M.-P., The Immunologist, 7, 132-136 (1999)/Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003)]. In the IMGT unique numbering, the conserved amino acids always have the same position, for instance cystein 23 (1st-CYS), tryptophan 41 (CONSERVED-TRP), hydrophobic amino acid 89, cystein 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become crucial information. The IMGT unique numbering is used in 2D graphical representations, designated as IMGT Colliers de Perles [Ruiz. M. and Lefranc. M.-P., Immunogenetics, 53, 857-883 (2002)/Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., T cell receptor and MHC structural data. Nucl. Acids. Res., 32, D208-D210 (2004)].

It must be understood that, without contradictory specification in the present specification, complementarity-determining regions or CDRs, mean the hypervariable regions of the heavy and light chains of immunoglobulins as defined according to the IMGT numbering system.

Nevertheless, CDRs can also be defined according to the Kabat numbering system (Kabat et al., Sequences of proteins of immunological interest, 5$^{th}$ Ed., U.S. Department of Health and Human Services, NIH, 1991, and later editions). There are three heavy-chain CDRs and three light-chain CDRs. Here, the terms "CDR" and "CDRs" are used to indicate, depending on the case, one or more, or even all, of the regions containing the majority of the amino acid residues responsible for the antibody's binding affinity for the antigen or epitope it recognizes. In order to simplify the reading of the present application, the CDRs according to Kabat are not defined. Nevertheless, it would be obvious for the person skilled in that art, using the definition of the CDRs according to IMGT, to define the CDRs according to Kabat.

In a particular embodiment, the IGF-1R antibody according to the invention is characterized in that it comprises a heavy chain variable domain of sequence SEQ ID No. 7, or any sequence with at least 90% of homology with the sequence SEQ ID No. 7.

In a particular embodiment, the IGF-1R antibody according to the invention is characterized in that it comprises a light chain variable domain of sequence SEQ ID No. 8, or any sequence with at least 90% of homology with the sequence SEQ ID No. 8.

According to still another embodiment, the antibody referred as 816C12, is characterized in that it comprises a heavy-chain variable domain sequence comprising the amino acid sequence SEQ ID No. 7 or a sequence with at least 80%, preferably 85%, 90%, 95% and 98% of homology after optimal alignment with sequence SEQ ID No. 7; and/or in that it comprises a light-chain variable domain sequence comprising the amino acid sequence SEQ ID No. 8 or a sequence with at least 80%, preferably 85%, 90%, 95% and 98% of homology after optimal alignment with sequence SEQ ID No. 8.

In the sense of the present invention, the "percentage of homology" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444] or by means of computer software using these algorithms (GAP, BESTFIT. FASTA and TFASTA in the Wisconsin Genetics Software Package, Genetics Computer Group, 575 Science Dr., Madison, Wis., or by the comparison software BLAST NR or BLAST P). For the amino acid sequence exhibiting at least 80%, preferably at least 85%, 90%, 95% and 98% of homology with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below.

Equivalent amino acids can be determined either on their structural homology with the amino acids for which they are substituted or on the results of comparative tests of biological activity between the various antigen binding proteins likely to be generated.

As a non-limiting example, table 1 below summarizes the possible substitutions likely to be carried out without resulting in a significant modification of the biological activity of the corresponding modified antigen binding protein; inverse substitutions are naturally possible under the same conditions.

TABLE 1

| Original residue | Substitution(s) |
| --- | --- |
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (E) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

A particular aspect of the invention is that the antibody, or any antigen binding fragment thereof, does not bind to the Insulin receptor (IR).

In another embodiment, the antibody of the invention consists of a monoclonal antibody.

The term "monoclonal antibody" or "Mab" as used herein refers to an antibody obtained from a population of substantially homogeneous antibodies, i.e. the individual antibodies of the population are identical except for possible naturally occurring mutations that may be present in minor amounts. Monoclonal antibodies are highly specific, being directed against a single epitope. Such monoclonal antibody may be produced by a single clone of B cells or hybridoma. Monoclonal antibodies may also be recombinant, i.e. produced by protein engineering. Monoclonal antibodies may also be isolated from phage antibody libraries. In addition, in contrast with preparations of polyclonal antibodies which typically include various antibodies directed against various determinants, or epitopes, each monoclonal antibody is directed against a single epitope of the antigen. The invention relates to an antibody isolated or obtained by purification from natural sources or obtained by genetic recombination or chemical synthesis.

In another embodiment, the antibody of the invention consists of a recombinant antibody. The term "recombinant antibody" refers to an antibody that results from the expression of recombinant DNA within living cells. A recombinant antibody of the invention is obtained by using laboratory methods of genetic recombination, well known by a person skilled in the art, creating DNA sequences that would not be found in biological organisms.

In another embodiment, the antibody of the invention consists of a chemically synthesized antibody.

"IGF-1R antibody" includes (without contrary specification) the murine, but also the chimeric and the humanized forms of the said IGF-1R antibody.

For more clarity, the following table 2 illustrates the sequences of the antibody 816C12, defined according to IMGT.

TABLE 2

| Antibody | CDR numbering | Heavy chain | Light chain | SEQ ID NO. |
| --- | --- | --- | --- | --- |
| 810D12I-4893 | IMGT | CDR-H1 | | 1 |
| | | CDR-H2 | | 2 |
| | | CDR-H3 | | 3 |
| | | | CDR-L1 | 4 |
| | | | CDR-L2 | 5 |
| | | | CDR-L3 | 6 |
| | | variable domain | | 7 |
| | | | variable domain | 8 |

In one embodiment, the monoclonal antibody herein includes murine, chimeric and humanized antibody. The antibody can be derived from an hybridoma of murine origin filed within the French collection for microorganism cultures (CNCM, Pasteur Institute, Paris, France), said hybridoma being obtained by the fusion of Balb/C immunized mice splenocytes/lymphocytes and cells of the myeloma Sp 2/O—Ag 14 cell line.

According to another aspect, the invention relates to a murine hybridoma capable of secreting a monoclonal antibody according to the invention, notably the hybridoma of murine origin deposited at the CNCM, Institut Pasteur, Paris, France, on Sep. 17, 2014, under the number 1-4894.

The monoclonal antibody, here referred as 816C12, or any antigen-binding fragment thereof, being secreted by the said hybridoma 1-4894 obviously forms part of the present invention.

The invention relates to an IGF-1R antibody, or an antigen-binding fragment thereof, characterized in that it is secreted by the hybridoma filed at the CNCM, Institut Pasteur, Paris, on Sep. 17, 2014, under number 1-4894.

The invention also describes the murine hybridoma filed at the CNCM, Institut Pasteur, Paris, on Sep. 17, 2014, under number 1-4894.

A novel aspect of the present invention relates to an isolated nucleic acid, characterized in that it is chosen from the following nucleic acids:

a) a nucleic acid coding for an antibody according to the invention;

b) a nucleic acid comprising a sequence selected from the sequences SEQ ID No.9 or 10, or a sequence with at least 80%, preferably 85%, 90%, 95% and 98% b of homology after optimal alignment with the sequences SEQ ID No. 9 or 10; and e) a complementary nucleic acids of the nucleic acids as defined in a) or b).

Table 3 below summarizes the various nucleotide sequences concerning the antibody 816C12 of the invention.

TABLE 3

| Antibody | Heavy chain | Light chain | SEQ ID NO. |
| --- | --- | --- | --- |
| 810D12I-4893 | variable domain | | 9 |
| | | variable domain | 10 |

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, defining a fragment or a region of a nucleic acid, containing unnatural nucleotides or not, and being either a double-strand DNA, a single-strand DNA or transcription products of said DNAs.

It should also be included here that the present invention does not relate to nucleotide sequences in their natural chromosomal environment, i.e., in a natural state. The sequences of the present invention have been isolated and/or purified, i.e., they were sampled directly or indirectly, for example by a copy, their environment having been at least partially modified. Isolated nucleic acids obtained by recombinant genetics, by means, for example, of host cells, or obtained by chemical synthesis should also be mentioned here.

The invention also relates to a vector comprising a nucleic acid as described in the invention.

The invention notably targets cloning and/or expression vectors that contain such a nucleotide sequence.

The vectors of the invention preferably contain elements which allow the expression and/or the secretion of nucleotide sequences in a given host cell. The vector thus must contain a promoter, translation initiation and termination signals, as well as suitable transcription regulation regions. It must be able to be maintained in a stable manner in the host cell and may optionally have specific signals which specify secretion of the translated protein. These various elements are selected and optimized by a person skilled in the art according to the host cell used. For this purpose, the nucleotide sequences can be inserted in self-replicating vectors within the chosen host or be integrative vectors of the chosen host.

Such vectors are prepared by methods typically used by a person skilled in the art and the resulting clones can be introduced into a suitable host by standard methods such as lipofection, electroporation, heat shock or chemical methods.

The vectors are, for example, vectors of plasmid or viral origin. They are used to transform host cells in order to clone or express the nucleotide sequences of the invention.

The invention also comprises host cells transformed by or comprising a vector as described in the present invention.

The host cell can be selected among prokaryotic or eukaryotic systems such as bacterial cells, for example, but also yeast cells or animal cells, notably mammal cells. Insect or plant cells can also be used.

The invention also relates to animals, other than man, that have a transformed cell according to the invention.

Another aspect of the invention relates to a method for the production of an antibody according to the invention, or one of its functional fragments, characterized in that said method comprises the following steps:
a) the culture in a medium of and the suitable culture conditions for a host cell according to the invention; and
b) the recovery of said antibody, or one of its functional fragments, thus produced from the culture medium or from said cultured cells.

The transformed cells according to the invention are of use in methods for the preparation of recombinant polypeptides according to the invention. Methods for the preparation of polypeptide according to the invention in recombinant form, characterized in that said methods use a vector and/or a cell transformed by a vector according to the invention, are also comprised in the present invention. Preferably, a cell transformed by a vector according to the invention is cultured under conditions that allow the expression of the aforesaid polypeptide and recovery of said recombinant peptide.

As already mentioned, the host cell can be selected among prokaryotic or eukaryotic systems. In particular, it is possible to identify the nucleotide sequences of the invention that facilitate secretion in such a prokaryotic or eukaryotic system. A vector according to the invention carrying such a sequence can thus be used advantageously for the production of recombinant proteins to be secreted. Indeed, the purification of these recombinant proteins of interest will be facilitated by the fact that they are present in the supernatant of the cellular culture rather than inside host cells.

The use of the antibody of the invention as biomarker is also disclosed. The methods may be used for detecting or diagnosing various hyperproliferative oncogenic disorders associated with expression of IGF-1R exemplified by, but not limited to, prostate cancer, osteosarcomas, lung cancer, breast cancer, endometrial cancer, glioblastoma, colon, cancer, gastric cancer, renal cancer, pancreas cancer, head and neck cancer or any other cancer associated with expression of IGF-1R. As would be recognized by one of ordinary skill in this art, the level of antibody expression associated with a particular disorder will vary depending on the nature and/or the severity of the pre-existing condition.

Administration of the antibodies of the present invention in any of the conventional ways known to one skilled in the art (e.g., topical, parenteral, intramuscular, etc.), will provide an extremely useful method of detecting dysplastic cells in a sample as well as allowing a clinician to monitor the therapeutic regiment of a patient undergoing treatment for a hyperproliferative disorder associated with or mediated by expression of IGF-1R.

The antibody of the invention, or an antigen-binding fragment thereof, will find use in various medical or research purposes, including the detection, diagnosis, prognosis and staging of various pathologies associated with expression of IGF-1R.

An embodiment of the invention relates to the IGF-1R antibody, or an antigen-binding fragment thereof, as above described for use as an agent for the detection of IGF-1R expressing tumoral cells.

Another embodiment of the invention is the IGF-1R antibody, or an antigen-binding fragment thereof, as above described, for use in the in vitro or ex vivo diagnosing or prognosing of an oncogenic disorder associated with expression of IGF-1R.

"Diagnosing" a disease as used herein refers to the process of identifying or detecting the presence of a pathological hyperproliferative oncogenic disorder associated with or mediated by expression of IGF-1R, monitoring the progression of the disease, and identifying or detecting cells or samples that are indicative of a disorder associated with the expression of IGF-1R.

"Prognosis" as used herein means the likelihood of recovery from a disease or the prediction of the probable development or outcome of a disease. For example, if a sample from a subject is negative for staining with the IGF-1R antibody, then the "prognosis" for that subject is better than if the sample is positive for IGF-1R staining. Samples may be scored for IGF-1R expression levels on an appropriate scale as it will be more detailed hereinafter.

The IGF-1R antibody can be present in the form of an immunoconjugate or of a labeled-antibody to obtain a detectable/quantifiable signal. When used with suitable labels or other appropriate detectable biomolecules or chemicals, the IGF-1R antibody is particularly useful for in vitro and in vivo diagnosis and prognosis applications.

Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA). Various types of labels and methods of conjugating the labels to the IGF-1R antibodies are well known to those skilled in the art, such as the ones set forth below.

As used herein, the term "an oncogenic disorder associated with expression of IGF-1R" is intended to include diseases and other disorders in which the presence of high levels of IGF-1R (aberrant) in a subject suffering from the disorder has been shown to be or is suspected of being either responsible for the pathophysiology of the disorder or a factor that contributes to a worsening of the disorder. Alternatively, such disorders may be evidenced, for example, by an increase in the levels of IGF-1R on the cell surface in the affected cells or tissues of a subject suffering from the disorder. The increase in IGF-1R levels may be detected using the IGF-1R antibody.

In certain embodiments, "increased expression" as it relates to IGF-1R refers to protein or gene expression levels that demonstrate a statistically significant increase in expression (as measured by RNA expression or protein expression) relative to a control.

An embodiment is an IGF-1R antibody, or an antigen-binding fragment thereof, as above described, for use in determining whether a patient with an oncogenic disorder is likely to benefit from treatment with an inhibitor targeting the IGF-1R pathway, preferentially an IGF-1R antibody alone, combined or conjugated.

As used in the present specification, the expression "inhibitor targeting the IGF-1R pathway" means any compound capable of decreasing or inhibiting the tyrosine kinase activity of IGF-1R, either by binding to the ligand(s) of IGF-IR or to the IGFR itself. Examples for such inhibitors are protein, peptides, antibodies or Antibody-Drug-Conjugates or any chemical compound which act as IGF-1R antagonists, antisense oligonucleotides or siRNA inhibiting expression of the IGF-1R gene or of a gene encoding one of the IGFR ligand(s), or any other drug or compound known by the person skilled in the art.

More particularly, in the sense of the present specification, the inhibitor targeting the IGF-1R pathway is intended to encompass any compound or molecule capable of binding to the IGF-1R and inhibiting the binding of its ligand(s).

Still more particularly, in the sense of the present specification, the inhibitor targeting the IGF-1R pathway is intended to encompass any monoclonal antibody which binds to the IGF-1R.

In another preferred embodiment, the inhibitor targeting the IGF-1R pathway consists of an Antibody-Drug-Conjugate (ADC) wherein the antibody moiety targets the IGF-1R and the Drug moiety can be selected from any drugs such as cytotoxic, cytostatic, toxins, etc. . . . . . In an exemplified embodiment, the drug moiety can consist of an auristatin, an analog or a derivative.

It is also an object of the invention to describe a method for detecting in vitro or ex vivo the presence and/or the location of IGF-1R expressing tumoral cells in a subject, said method comprising the steps of:

(a) contacting a biological sample from the said subject with the IGF-1R antibody, or an antigen-binding fragment thereof, according to the present invention as above described; and (b) detecting the binding of the said IGF-1R antibody, or an antigen-binding fragment thereof, with the said biological sample.

The present invention is also directed to an in vitro or ex vivo method for detecting and/or to quantify and/or to determine the level of, the expression of IGF-1R in, preferably at the surface of cells of, a subject, said method comprising the steps of:

(a) contacting a biological sample from the said subject with the IGF-1R antibody, or an antigen-binding fragment thereof, according to the present invention as above described; and (b) detecting, and/or quantifying, and/or determining the level of, the binding of the said IGF-1R antibody, or an antigen-binding fragment thereof, with the said biological sample.

The binding of the IGF-1R antibody may be detected and/or quantified and/or determined by various assays available to the skilled artisan. Although any suitable means for carrying out the assays are included within the invention, Fluorescence Activated Cell Sorting (FACS). ELISA, western blotting and immunohistochemistry (IHC) can be mentioned in particular. Preferred methods include IHC and FACS.

The invention also describes a method for detecting in vitro or ex vivo the percentage of tumoral cells expressing IGF-1R in a subject, said method comprising the steps of:

(a) contacting a biological sample from the said subject with the IGF-1R antibody, or an antigen-binding fragment thereof, as above described; and (b) quantifying the percentage of cells expressing IGF-1R in the biological sample.

Another embodiment is a method for determining in vitro or ex vivo the expression level of IGF-1R in tumoral cells or in a tumor in a subject, said method comprising the steps of:

(a) contacting a biological sample from the said subject with the IGF-1R antibody, or an antigen-binding fragment thereof, as above described; and (b) quantifying the level of binding of the said IGF-1R antibody, or an antigen-binding fragment thereof, to IGF-1R in the said biological sample.

As will be apparent to the skilled artisan, the level of IGF-1R antibody binding to IGF-1R may be quantified by any means known to the person of skills in the art. Preferred methods involve the use of immunoenzymatic processes, such as ELISA assays, immunofluorescence, IHC, radio-immunoassay (RIA), or FACS.

According to the method of the invention, the level of binding of the said IGF-1R antibody, or an antigen-binding fragment thereof, to IGF-1R is quantified by Fluorescence Activated Cell Sorting (FACS) or immunohistochemistry (IHC).

A "biological sample" may be any sample that may be taken from a subject. Such a sample must allow for the determination of the expression levels of the biomarker of the invention. The nature of the sample will thus be dependent upon the nature of the tumor.

Preferred biological samples include samples such as a blood sample, a plasma sample, or a lymph sample, if the cancer is a liquid tumor.

Preferred biological samples include samples such as a biopsy sample or a sample taken from a surgical resection therapy, if the cancer is a solid tumor.

Preferably, the biological sample is a biological fluid, such as serum, whole blood cells, a tissue sample or a biopsy of human origin. The sample may for example include, biopsied tissue, which can be conveniently assayed for the presence of a pathological oncogenic disorder associated with expression of IGF-1R.

Once a determination is made of the IGF-1R expression level in the tested biological samples, the results can be compared with those of control samples, which are obtained in a manner similar to the tested biological samples but from individuals that do not have an oncogenic disorder associated with expression of IGF-1R. If the level of IGF-1R is significantly elevated in the tested biological sample, it may be concluded that there is an increased likelihood of the subject from which it was derived has or will develop said disorder.

The invention relates to a process of in vitro or ex vivo diagnosis or prognosis of an IGF-1R expressing tumor, wherein said process comprises the steps of (i) determining the expression level of IGF-1R by the a method for determining in vitro or ex vivo the expression level of IGF-1R in tumoral cells or in a tumor in a subject according to the present invention and as above described, and (ii) comparing the expression level of step (i) with a reference expression level of IGF-1R from normal tissue or a non expressing IGF-1R tissue.

With regards to the development of targeted antitumor therapy, the diagnosis with immunohistological techniques gives in situ information on the receptor expression level and thus enables to select patients susceptible to be treated following the expression level of receptors needed for such treatment.

Stage determination has potential prognosis value and provides criteria for designing optimal therapy. Simpson et al., J. Clin. Oncology 18:2059 (2000). For example, treatment selection for solid tumors is based on tumor staging, which is usually performed using the Tumor/Node/Metastasis (TNM) test from the American Joint Committee on Cancer (AJCC). It is commonly acknowledged that, while this test and staging system provides some valuable information concerning the stage at which solid cancer has been diagnosed in the patient, it is imprecise and insufficient. In particular, it fails to identify the earliest stages of tumor progression.

Another embodiment consists of a method for determining in vitro or ex vivo the IGF-1R scoring of tumoral cells or of the tumor in a subject, said method comprising the steps of:

(a) contacting a biological sample from the said subject with the IGF-1R antibody, or an antigen-binding fragment thereof, as above described;

(b) quantifying by Fluorescence Activated Cell Sorting (FACS) or immunohistochemistry (IHC) the level of binding of the said IGF-1R antibody, or an antigen-binding fragment thereof, to IGF-1R in the said biological sample; and (c) scoring the tumoral cells or the tumor by comparing the quantified level obtained in step (b) to an appropriate scale based on two parameters which are the intensity of the staining and the percentage of positive cells.

In an embodiment, the IGF-1R antibody is capable of binding IGF-1R when tissue samples are, formalin fixed-, formol substituted fixed-, Glyco-fixx fixed-, paraffin embedded and/or frozen.

Any conventional hazard analysis method may be used to estimate the prognostic value of IGF-1R. Representative analysis methods include Cox regression analysis, which is a semiparametric method for modeling survival or time-to-event data in the presence of censored cases (Hosmer and Lemeshow, 1999: Cox, 1972). In contrast to other survival analyses, e.g. Life Tables or Kaplan-Meyer, Cox allows the inclusion of predictor variables (covariates) in the models. Using a convention analysis method, e.g., Cox one may be able to test hypotheses regarding the correlation of IGF-1R expression status of in a primary tumor to time-to-onset of either disease relapse (disease-free survival time, or time to metastatic disease), or time to death from the disease (overall survival time). Cox regression analysis is also known as Cox proportional hazard analysis. This method is standard for testing the prognostic value of a tumor marker on patient survival time. When used in multivariate mode, the effect of several covariates are tested in parallel so that individual covariates that have independent prognostic value can be identified, i.e. the most useful markers. The term negative or positive "IGF-1R status" can also be referred as [IGF-1R (−)] or [IGF-1R (+)].

A sample may be "scored" during the diagnosis or monitoring of cancer. In its simplest form, scoring may be categorical negative or positive as judged by visual examination of samples by immunohistochemistry. More quantitative scoring involves judging the two parameters intensity of staining and the proportion of stained ("positive") cells that are sampled.

"IGF-1R status" within the meaning of the invention, relates to the classification of tumor to a IGF-1R positive [IGF-1R (+)] or IGF-1R negative [IGF-1R (−)] class based on the determination of the expression level of the IGF-IR as measured by any methods such as immunohistochemistry (IHC), Fluorescence Activated Cell Sorting FACS, or other methods known by the person skilled in the art.

In an embodiment, to ensure standardization, samples may be scored for IGF-1R expression levels on different scales, most of them being based on an assessment of the intensity of the reaction product and the percentage of positive cells (Payne et al., Predictive markers in breast cancer—the present, Histopathology 2008, 52, 82-90).

In another embodiment, said scoring, particularly in step (c) of the method of the present invention, comprises using an appropriate scale based on the intensity of the staining and the percentage of positive cells.

As a first example, by analogy with the Quick Allred scoring for IHC assessment of oestrogen receptor and progesterone receptor, samples may be scored for IGF-1R expression levels on a global scale from 0 to 8 combining scores for intensity of reactivity and for the proportion of cells stained (Harvey J M. Clarck G M, Osborne C K. Allred D C; J. Clin. Oncol. 1999: 17; 1474-1481). More particularly, the first criteria of intensity of reactivity is scored on a scale from 0 to 3, 0 corresponding to "No reactivity" and 3 corresponding to "Strong reactivity". The second criteria of proportion reactive is scored on a scale from 0 to 5, 0 corresponding to "No reactivity" and 5 to "67-100% proportion reactive". The intensity of the reactivity score and the proportion reactive score are then summed to produce total score of 0 through 8. A total score of 0-2 is regarded as negative while a total score of 3-8 is regarded as positive.

According to this scale, the terms negative or positive "IGF-1R status" of tumors or of tumoral cells used in the present description refers to levels of expression of IGF-1R that correspond to scores 0-2 or 3-8 on the Allred scale, respectively.

Table 4 hereinafter illustrates the guidelines for interpreting IHC results according to Allred method.

TABLE 4

| Intensity of immunoreactivity | Score 1 | Proportion reactive | Score 2 |
|---|---|---|---|
| No reactivity | 0 | No reactivity | 0 |
| Weak reactivity | 1 | <1% | 1 |
| Moderate reactivity | 2 | 1-10% | 2 |
| Strong reactivity | 3 | 11-33% | 3 |
| — | | 34-66% | 4 |
| — | | 67-100% | 5 |

| Total Score (Score 1 + Score 2) | Interpretation |
|---|---|
| 0-2 | Negative |
| 3-8 | Positive |

According to the invention, the method is characterized in that the said appropriate scale is a scale of 0 to 8 wherein no reactivity is scored 0, and a strong reactivity in a proportion of 67-100% proportion reactive is scored 8.

Thus, in a preferred embodiment, the method for determining in vitro or ex vivo the IGF-1R scoring of tumoral cells or of a tumor in a subject according to the present invention, is characterized in that in step (c) the said appropriate scale is a scale of 0 to 8 wherein no reactivity is scored 0, and a strong reactivity in a proportion of 67-100% proportion reactive is scored 8.

In other words, it is described and claimed a process of determining in vitro or ex vivo the status of a tumor or of tumoral cells from a subject, wherein said process comprises the steps of:
(a) scoring a tumor or of tumoral cells from a subject according to the Allred scale; and
(b)—i) determining that the status of the tumor or of tumoral cells is [IGF-1R(+)] with an Allred score of 3 to 8; or
ii) determining that the status of the tumor or of tumoral cells is [IGF-IR(−)] with an Allred score of 0 to 2.

In a particular aspect of the invention, the status of the tumor or of tumoral cells is [IGF-1R (+)] with an Allred score of 3.

In a particular aspect of the invention, the status of the tumor or of tumoral cells is [IGF-1R (+)] with an Allred score of 4.

In a particular aspect of the invention, the status of the tumor or of tumoral cells is [IGF-1R (+)] with an Allred score of 5.

In a particular aspect of the invention, the status of the tumor or of tumoral cells is [IGF-1R (+)] with an Allred score of 6.

In a particular aspect of the invention, the status of the tumor or of tumoral cells is [IGF-1R (+)] with an Allred score of 7.

In a particular aspect of the invention, the status of the tumor or of tumoral cells is [IGF-1R (+)] with an Allred score of 8.

In another particular aspect of the invention, the status of the tumor or of tumoral cells is [IGF-1R (+)] with an Allred score of 3 to 8.

Another particular method herein described for determining in vitro or ex vivo the IGF-1R status of tumoral cells or of the tumor in a subject, is characterized in that it comprises the steps of:
(a) scoring IGF-1R tumoral cells or of the tumor from the said subject according to the method of the claim 18; and
(b) determining that the IGF-1R status of tumoral cells or of the tumor is [IGF-1R(+)] with a score of 3 to 8; or
(c) determining that the IGF-1R status of tumoral cells or of the tumor is [IGF-1R(−)] with a score of 0 to 2.

As a second example, by analogy with the conventional scoring for IHC assessment of HER-2 receptor for example, samples may be scored for IGF-1R expression levels on a somewhat simpler scoring method integrating the intensity of staining (preferentially membranous staining) and the proportion of cells that display staining into a combined scale from 0 to 3+.

In this scale, referred as the simplified scale, 0 and 1+ are negative whereas 2+ and 3+ represents positive staining. Nevertheless, scores 1+-3+ can be recoded as positive because each positive score may be associated with significantly higher risk for relapse and fatal disease when compared to score 0 (negative), but increasing intensity among the positive scores may provide additional risk reduction.

Generally speaking, the terms negative or positive "IGF-1R status" of tumors or of tumoral cells used in the present description refers to levels of expression of IGF-1R that correspond to scores 0-1+ or 2+-3+ on the simplified scale, respectively. Only complete circumferential membranous reactivity of the invasive tumor should be considered and often resembled a "chicken wire" appearance. Under current guidelines, samples scored as borderline (score of 2+ or 3+) for IGF-1R are required to undergo further assessment. The IHC analysis should be rejected, and either repeated or tested by FISH or any other method if, as non limitative example, controls are not as expected, artifacts involve most of the sample and the sample has strong membranous positivity of normal breast ducts (internal controls) suggesting excessive antigen retrieval.

For more clarity, table 5 hereinafter summarizes these parameters.

TABLE 5

| IGF-1R status | IHC description |
|---|---|
| 0 | No reactivity or membranous reactivity in less than 10% of tumour cells |
| 1+ | Faint/barely perceptible membranous reactivity is detected in more than 10% of tumour cells. The cells are immunoreactive only in part of the membrane. |
| 2+ | Weak to moderate complete membranous reactivity is seen in more than 10% of tumour cells. |
| 3+ | Strong complete reactivity is seen in more than 10% of tumour cells. |

The method of the invention is characterized in that the said appropriate scale is a scale of 0 to 3+ wherein no membranous reactivity of tumor cells is scored 0 and strong complete reactivity in more than 10% of tumor cells is scored 3+.

In more details, as above described, said appropriate scale is a scale of 0 to 3 wherein no membranous reactivity of tumor cells is scored 0; faint perceptible membranous reactivity in more than 10% of tumor cells is scored 1+; weak to moderate complete membranous reactivity in more than 10% of tumor cells is scored 2+; and strong complete reactivity in more than 10% of tumor cells is scored 3+.

In other words, it is described and claimed a process of determining in vitro or ex vivo the status of a tumor of tumoral cells from a subject, wherein said process comprises the steps of (a) scoring a tumor or tumoral cells from a subject according to the simplified scale as above described; and (b) determining that the status of the tumor or of tumoral cells is [IGF-1R(+)] with a score of 2+ or 3+; or (c)

determining that the status of the tumor or of tumoral cells is [IGF-1R(−)] with a score of 0 or 1+.

In a particular aspect of the invention, a tumor or tumoral cells is [IGF-1R (+)] with a score of 2+.

In a particular aspect of the invention, a tumor is, or tumoral cells are [IGF-1R (+)] with a score of 3+.

In another particular aspect of the invention, a tumor is, or tumoral cells are [IGF-1R (+)] with a score of 2+ or 3+.

In another embodiment, the invention relates to a method for determining in vitro or ex vivo the IGF-1R status tumoral cells or a tumor in a subject, said method comprising the steps of:

(a) scoring said IGF-1R tumoral cells or said tumor from the said subject according to the method of the present invention described before; and (b)—i) determining that the IGF-1R status of tumoral cells or of the tumor is [IGF-1R(+)] with a score of $2^+$ or $3^+$; or
    ii) determining that the IGF-1R status of tumoral cells is [IGF-1R(−)] with a score of 0 or $1^+$.

Generally, the results of a test or assay can be presented in any of a variety of formats. The results can be presented qualitatively. For example, the test report may indicate only whether or not a particular polypeptide was detected, perhaps also with an indication of the limits of detection. The results may be displayed as semi-quantitative. For example, various ranges may be defined, and the ranges may be assigned a score (e.g., 0 to 3+ or 0 to 8 depending on the used scale) that provides a certain degree of quantitative information. Such a score may reflect various factors, e.g., the number of cells in which IGF-1R is detected, the intensity of the signal (which may indicate the level of expression of IGF-1R or IGF-1R-bearing cells), etc. The results may be displayed in a quantitative way, e.g., as a percentage of cells in which IGF-1R is detected, as a protein concentration, etc.

As will be appreciated by one of ordinary skill in the art, the type of output provided by a test will vary depending upon the technical limitations of the test and the biological significance associated with detection of the polypeptide. For example, in the case of certain polypeptides a purely qualitative output (e.g., whether or not the polypeptide is detected at a certain detection level) provides significant information. In other cases a more quantitative output (e.g., a ratio of the level of expression of the polypeptide in the sample being tested versus the normal level) is necessary.

In another aspect, it is described a method of diagnosing pathological hyperproliferative oncogenic disorder or a susceptibility to a pathological condition associated with expression of IGF-1R in a subject, said method comprising the steps of:

(a) determining the presence or absence of IGF-1R carrying cells in a sample by a method for the detection of IGF-1R expressing cells and/or for determining the level of expression of IGF-1R according to the present invention, and (b) diagnosing a pathological condition or susceptibility to a pathological condition based on the presence or absence of said IGF-1R bearing cells.

In the methods herein described, the detection of IGF-1R expressing cells or an increase in the levels of IGF-1R is generally indicative of a patient with or suspected of presenting a IGF-1R mediated disorder.

The present invention also provides a method for predicting the risk of an individual to develop a cancer, said method comprising detecting the expression level of IGF-1R in a tissue sample by a method for the detection of IGF-1R expressing cells and/or for determining the level of expression of IGF-1R according to the present invention, wherein a high level of IGF-1R expression is indicative of a high risk of developing a cancer.

The invention also relates to a method for evaluating tumor aggressiveness.

"Tumor aggressiveness" as used herein refers to a tumor quickly growing and tending to spread rapidly.

In one embodiment, the said method for evaluating tumor aggressiveness comprises the step of:

(a) determining the level of IGF-1R expressed by cells in a tumor sample, by a method for the detection of IGF-1R expressing cells and/or for determining the level of expression of IGF-1R according to the present invention.

(b) determining the level of IGF-1R expressed in an equivalent tissue sample taken from the same individual at a later time by a method for the detection of IGF-1R expressing cells and/or for determining the level of expression of IGF-1R according to the present invention, and (c) determining the ratio between the expression level obtained in step (a) and the ratio obtained in step (b) wherein the ratio of IGF-1R expression in the tumor sample over time provides information on the risks of cancer progression.

In a preferred embodiment, a ratio of the level obtained in step (a) to the level obtained in step (b) greater than 1 indicates aggressiveness. In another embodiment, a ratio inferior or equal to 1 indicates non aggressiveness.

Another aspect of the invention is the monitoring of IGF-1R expression in response to the administration of a therapy targeting the IGF-1R pathway by involving the method for the detection of, and/or to quantify IGF-1R and/or to determine the level of, expression according to the present invention. Such a monitoring can be very useful when the said therapy triggers the downregulation and/or the degradation of IGF-1R.

It is also an object of the invention to describe a method for determining whether an oncogenic disorder is susceptible to treatment with an antibody drug targeting the IGF-1R pathway, said method comprising the steps of:

(a) determining in vitro or ex vivo the IGF-1R status of tumoral cells of a tumor of a subject according to the method of scoring of the present invention as above described, and (b) determining that, if the IGF-1R status of tumoral cells or of the tumor is IGF-1R(+), the oncogenic disorder is susceptible to treatment with an antibody drug targeting the IGF-1R pathway.

In particular, monitoring IGF-1R expression on the cell surface could be a critical tool for evaluating the efficacy of the treatment during clinical trials and "personalized" therapies.

The application thus provides methods for determining the appropriate therapeutic regimen for a subject.

An increase or a decrease in the level of IGF-1R which can be determined by the method for the detection of and/or to determine the level of, expression according to the present invention, is indicative of the evolution of a cancer associated with IGF-1R. Thus, by measuring an increase in the number of cells expressing IGF-1R or changes in the concentration of IGF-1R present in various tissues or cells, it is possible to determine whether a particular therapeutic regime aimed at ameliorating a malignancy associated with IGF-1R is effective.

Another object of the invention is also a method for determining in vitro or ex vivo the efficacy of a therapeutic regimen designed to alleviate an oncogenic disorder associated with IGF-1R in a subject suffering from said disorder, said method comprising the steps of:

(a) determining a first expression level of IGF-1R by the method for the detection of and/or to determine the level of, expression according to the present invention, as above described in a first biological sample, said first biological sample corresponding to first time point of the said treatment;

(b) determining a second expression level of IGF-1R by the method for the detection of and/or to determine the level of, expression according to the present invention, as above described in a second biological sample, said second biological sample corresponding to a second, later time point of the said treatment;

(c) calculating the ratio of the said first expression level obtained in step (a) to the said second expression level obtained in step (b); and (d) determining that the efficacy of said therapeutic regime is high when the ratio of step (c) is greater than 1; or determining that the efficacy of said therapeutic regime is low when the ratio of step (c) is inferior or equal to 1.

In a preferred embodiment, the said therapeutic regime designed to alleviate an oncogenic disorder associated with IGF-1R in a subject suffering from said disorder includes the administration of a therapy targeting the IGF-1R pathway to the said subject.

It is also an object of the invention to provide an in vivo method of imaging an oncogenic disorder associated with expression of IGF-1R using the method for the detection of and/or to determine the level of, expression according to the present invention. Such a method is useful for localizing in vivo the tumoral cells, as well as monitoring their invasiveness. Likewise, the method is useful for monitoring the progression and/or the response to treatment in patients previously diagnosed with a IGF-1R-mediated cancer.

An embodiment is a method for detecting the location of IGF-1R expressing tumoral cells in a subject, said method comprising the steps of:

a) administering the IGF-1R antibody, or a antigen-binding fragment thereof, according to the present invention to the subject; and b) detecting binding of said IGF-1R antibody, wherein said binding indicates the presence of the tumoral cells.

As for the detection of the presence of an expressing tumor, many techniques known by the person skilled in the art can be used. Nevertheless, preferred means are IHC and FACS.

In another aspect, the invention provides an in vivo imaging reagent, the said reagent comprising the IGF-1R antibody, or an antigen-binding fragment thereof, according to the present invention, the said IGF-1R antibody being preferably labeled, more preferably radiolabeled.

The present invention also contemplates the use of the said reagent in medical imaging of a patient suffering from an IGF-1R-mediated cancer.

The method of the invention comprises the steps of:

(a) administering to the said patient an imaging-effective amount of an imaging reagent of the invention and (b) detecting the said reagent.

In a preferred embodiment, the imaging agent comprises the IGF-1R antibody, or an antigen-binding fragment thereof, according to the present invention, and an active moiety.

An "active moiety" as used herein is an agent which permits in vivo detection of the said imaging reagent. The active moiety according to the invention includes in particular radio-elements such as Technetium-99m (99mTc), Copper-67 (Cu-67). Scandium-47 (Sc-47), Luthetium-77 (Lu-177) copper-64 (Cu-64), Yttrium-86 (Y-86) or Iodine-124 (1-124).

The imaging agent is administered in an amount effective for diagnostic use in a mammal such as a human and the localization and accumulation of the imaging agent is then detected. The localization and accumulation of the imaging agent may be detected by radionucleide imaging, radioscintigraphy, nuclear magnetic resonance imaging, computed tomography, positron emission tomography, computerized axial tomography, X-ray or magnetic resonance imaging method, fluorescence detection, and chemiluminescent detection.

With regards to the development of targeted antitumor therapy, the diagnosis with immunohistological techniques gives in situ information on the receptor expression level, e.g. as regards the size and/or the location of the tumor. The diagnosis thus enables to select patients susceptible to be treated following the expression level of receptors needed for such a treatment.

A particular interesting aspect of the invention is a method for selecting a cancer patient predicted to benefit or not from the administration of a therapeutic amount of an antibody drug targeting the IGF-1R pathway, said method comprising the steps of:

(a) determining the expression level of IGF-1R according to the method of the invention above described:

(b) comparing the expression level of the previous step (a) with a reference expression level; and (c) selecting the patient as being predicted to benefit from a treatment with an antibody drug targeting the IGF-1R pathway, if the ratio of the expression level obtained in (a) to the reference expression level is greater than 1; or (d) selecting the patient as being not predicted to benefit from a treatment with an antibody drug targeting the IGF-1R pathway, if the ratio of the expression level obtained in (a) to the reference expression level is inferior or equal to 1.

The expression level of IGF-1R is advantageously compared or measured in relation to levels in a control cell or sample also referred to as a "reference level" or "reference expression level". "Reference level", "reference expression level", "control level" and "control" are used interchangeably in the specification. A "control level" means a separate baseline level measured in a comparable control cell, which is generally disease or cancer free. The said control cell may be from the same individual, since, even in a cancerous patient, the tissue which is the site of the tumor still comprises non tumor healthy tissue. It may also originate from another individual who is normal or does not present with the same disease from which the diseased or test sample is obtained. Within the context of the present invention, the term "reference level" refers to a "control level" of expression of IGF-1R used to evaluate a test level of expression of IGF-1R in a cancer cell containing sample of a patient. For example, when the level of IGF-1R in the biological sample of a patient is higher than the reference level of IGF-1R, the cells will be considered to have a high level of expression, or overexpression, of IGF-1R. The reference level can be determined by a plurality of methods. Expression levels may thus define IGF-1R bearing cells or alternatively the level of expression of IGF-1R independent of the number of cells expressing IGF-1R. Thus the reference level for each patient can be prescribed by a reference ratio of IGF-1R, wherein the reference ratio can be determined by any of the methods for determining the reference levels described herein.

For example, the control may be a predetermined value, which can take a variety of forms. It can be a single cut-off value, such as a median or mean. The "reference level" can be a single number, equally applicable to every patient individually, or the reference level can vary, according to specific subpopulations of patients. Thus, for example, older men might have a different reference level than younger men for the same cancer, and women might have a different reference level than men for the same cancer. Alternatively, the "reference level" can be determined by measuring the level of expression of IGF-1R in non-oncogenic cancer cells from the same tissue as the tissue of the neoplastic cells to be tested. As well, the "reference level" might be a certain ratio of IGF-1R in the neoplastic cells of a patient relative to the IGF-1R levels in non-tumor cells within the same patient. The "reference level" can also be a level of IGF-1R of in vitro cultured cells, which can be manipulated to simulate tumor cells, or can be manipulated in any other manner which yields expression levels which accurately determine the reference level. On the other hand, the "reference level" can be established based upon comparative groups, such as in groups not having elevated IGF-1R levels and groups having elevated IGF-1R levels. Another example of comparative groups would be groups having a particular disease, condition or symptoms and groups without the disease. The predetermined value can be arranged, for example, where a tested population is divided equally (or unequally) into groups, such as a low-risk group, a medium-risk group and a high-risk group.

The reference level can also be determined by comparison of the level of IGF-1R in populations of patients having the same cancer. This can be accomplished, for example, by histogram analysis, in which an entire cohort of patients are graphically presented, wherein a first axis represents the level of IGF-1R, and a second axis represents the number of patients in the cohort whose tumor cells express IGF-1R at a given level. Two or more separate groups of patients can be determined by identification of subsets populations of the cohort which have the same or similar levels of IGF-1R. Determination of the reference level can then be made based on a level which best distinguishes these separate groups. A reference level also can represent the levels of two or more markers, one of which is IGF-1R. Two or more markers can be represented, for example, by a ratio of values for levels of each marker.

Likewise, an apparently healthy population will have a different 'normal' range than will have a population which is known to have a condition associated with expression of IGF-1R. Accordingly, the predetermined value selected may take into account the category in which an individual falls. Appropriate ranges and categories can be selected with no more than routine experimentation by those of ordinary skill in the art. By "elevated" "increased" it is meant high relative to a selected control. Typically the control will be based on apparently healthy normal individuals in an appropriate age bracket.

It will also be understood that the controls according to the invention may be, in addition to predetermined values, samples of materials tested in parallel with the experimental materials. Examples include tissue or cells obtained at the same time from the same subject, for example, parts of a single biopsy, or parts of a single cell sample from the subject.

In another embodiment, the invention relates to a pharmaceutical composition for in vivo imaging of an oncogenic disorder associated with expression of IGF-1R comprising the IGF-1R antibody, or an antigen-binding fragment thereof, according to the present invention above described, or an antigen binding fragment thereof, which is labeled and a pharmaceutically acceptable carrier.

In another aspect, it is also described a kit for the detection of IGF-1R expressing tumoral cells in a patient, characterized in that said kit comprises at least the IGF-1R antibody, or an antigen-binding fragment thereof, as above described, and preferentially the antibody 816C212.

Packaged materials comprising a combination of reagents in predetermined amounts with instructions for performing the diagnostic assay. e.g. kits, are also within the scope of the invention. The kit contains the IGF-1R antibodies for detection and quantification of IGF-1R in vitro, e.g. in an ELISA. Where the IGF-1R antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. Such a kit may comprise a receptacle being compartmentalized to receive one or more containers such as vials, tubes and the like, such containers holding separate elements of the invention. For example, one container may contain a first antibody bound to an insoluble or partly soluble carrier. A second container may contain soluble, detectably-labeled second antibody, in lyophilized form or in solution. The receptacle may also contain a third container holding a detectably labeled third antibody in lyophilized form or in solution. A kit of this nature can be used in the sandwich assay of the invention. The label or package insert may provide a description of the composition as well as instructions for the intended in vitro or diagnostic use.

The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

In yet a further aspect, IGF-1R antibodies or antigen-binding fragments thereof as detailed herein according to the present invention, are provided labeled with a detectable moiety, such that they may be packaged and used, for example, in kits, to diagnose or identify cells having the aforementioned antigen. Non-limiting examples of such labels include fluorophores such as fluorescein isothiocyanate; chromophores, radionuclides, biotine or enzymes. Such labeled IGF-1R antibodies may be used for the histological localization of the antigen, ELISA, cell sorting, as well as other immunological techniques for detecting or quantifying IGF-1R, and cells bearing this antigen, for example.

The present invention is also directed to a kit, wherein said kit is characterized in that it comprises an IGF-1R antibody or antigen-binding fragments thereof, according to the present invention.

The present invention is also directed to a kit, wherein said kit is characterized in that it comprises a chimeric or humanized IGF-1R antibody or antigen-binding fragments thereof, which can be obtained from the 6 CDRs having the sequences SEQ ID Nos. 1 to 6 of the IGF-1R antibody or antigen-binding fragments thereof, according to the present invention.

Kits are also provided that are useful as a positive control for purification or immunoprecipitation of IGF-1R from cells. For isolation and purification of IGF-1R the kit can contain the IGF-1R antibody or antigen-binding fragments thereof as detailed herein according to the present invention coupled to beads (e.g., sepharose beads). Kits can be provided which contain the antibodies for detection and quantitation of IGF-1R in vitro, e.g. in an ELISA. The kit comprises a container and a label or package insert on or associated with the container. Additional containers may be included that contain, e.g., diluents and buffers, control antibodies. The label or package insert may provide a description of the composition as well as instructions for the intended in vitro or diagnostic use.

More particularly, the invention concerns a kit for the in vitro or ex vivo determination of the IGF-1R status of tumoral cells of a tumor in a subject by the methods herein described. In a preferred embodiment, as it will be described in the example, the invention relates to a kit for the determination of the IGF-1R status of a tumor or of tumoral cells by IHC and/or FACS methods.

In a particular embodiment, the invention consists in a kit comprising at least the IGF-1R antibody, or an antigen-binding fragment thereof, of the present invention as above described, said antibody being labeled.

In a preferred embodiment, the kit according to the invention further comprises a reagent useful for detecting the extent of binding between the said IGF-1R antibody and IGF-1R.

In another preferred embodiment, the kit of the invention useful for determining in vitro or ex vivo the expression level of IGF-1R in a IGF-1R-expressing tumor, further comprises a reagent useful for quantifying the level of binding between the said labeled IGF-1R antibody and IGF-1R.

In still another embodiment, the kit according to the invention further comprises: i) a reagent useful for detecting the extent of binding between the said labeled IGF-1R antibody and IGF-1R; and ii) positive and negative control samples useful for the scoring the IGF-1R expression level.

Said kit can further comprise a polyclonal antibody specific to murine antibodies or to human/humanized antibodies, preferably said polyclonal antibody specific to murine, humanized or human antibodies is labeled.

According to a particular embodiment of the invention, the kit for selecting in vitro a cancer patient who is predicted to benefit or not benefit from therapeutic administration of an inhibitor targeting the IGF-1R pathway can comprise: i) a reagent useful for detecting the extent of binding between the said IGF-1R antibody and IGF-1R; ii) control level that has been correlated with sensitivity to a IGF-1R inhibitor and/or iii) control level that has been correlated with resistance to a IGF-1R inhibitor.

The invention also relates to a kit for determining whether a patient with an oncogenic disorder is likely to benefit from treatment with an antibody drug targeting the IGF-1R pathway, characterized in that said kit comprises at least the IGF-1R antibody, or an antigen-binding fragment thereof, of the present invention as above described.

In another embodiment, said kit according is characterized in that it further comprises
i) a reagent for detecting the extent of binding between the said IGF-1R antibody and IGF-1R on the surface of tumoral cells; and/or
ii) a reagent for quantifying the level of binding between the said IGF-1R antibody and IGF-1R on the surface of tumoral cells.

Other characteristics and advantages of the invention appear in the continuation of the description with the examples and the figures whose legends are represented below.

FIG. 1: Graphic representation of OD values obtained with 816C12 antibody in the rhIGF1R ELISA. Data fitting and $EC_{50}$ determination are determined using Prism application.

Figure 2A:
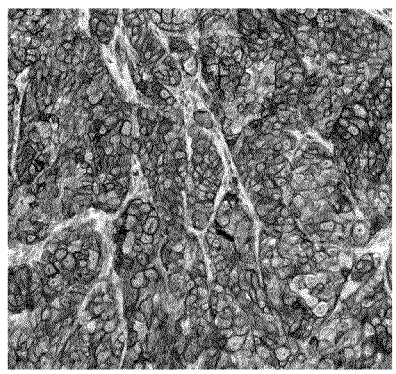
Figure 2B:
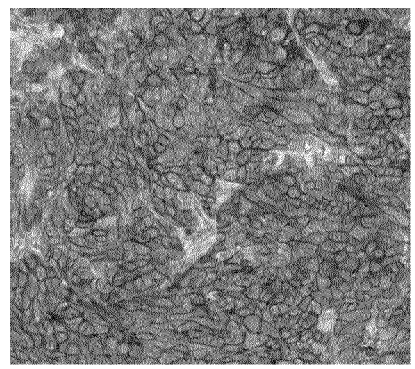
Figure 2C:
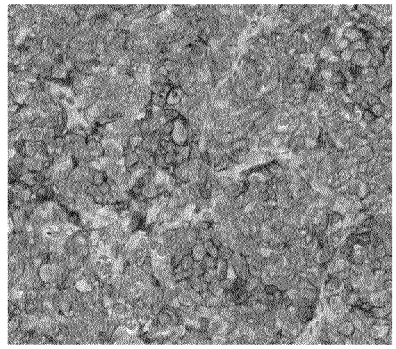

FIGS. 2A-2C: Immunohistochemistry (IHC) patterns of recognition of paraffin embedded tumor MCF-7 with the 816C12 (FIG. 2A), with G11 anti-IGF-1R antibody (Roche Ventana) (FIG. 2B) or AF-305 (R&D system) anti-IGF-1R antibody (FIG. 2C).

Figure 3:
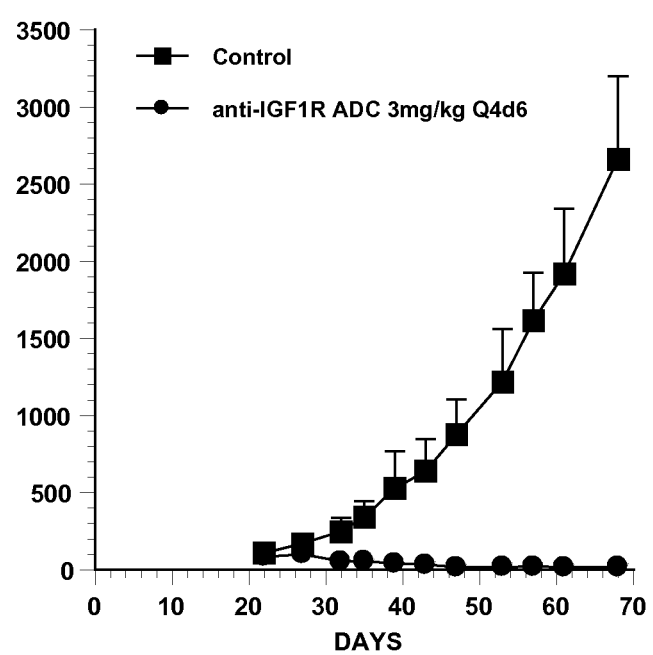

FIG. 3: In vivo activity of an anti-IGF-1R ADC in the MCF-7 xenograft model.

Figure 4A:
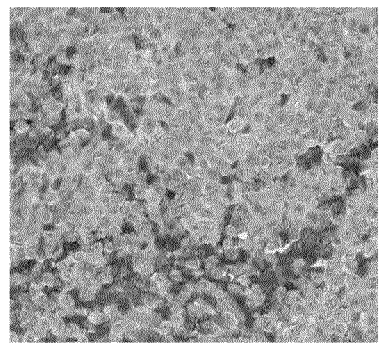
Figure 4B:
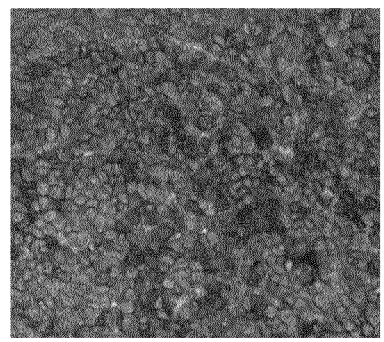
Figure 4C:
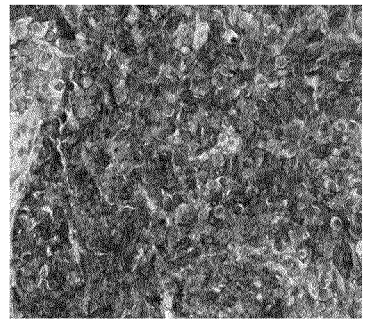

FIGS. 4A-4C: Immunohistochemistry (IHC) patterns of recognition of paraffin embedded tumor SBC-5 with the 816C12, with G11 anti-IGF-1R antibody (Roche Ventana) (FIG. 4B) or AF-305 (R&D system) anti-IGF-1R antibody (FIG. 4C).

Figure 5:
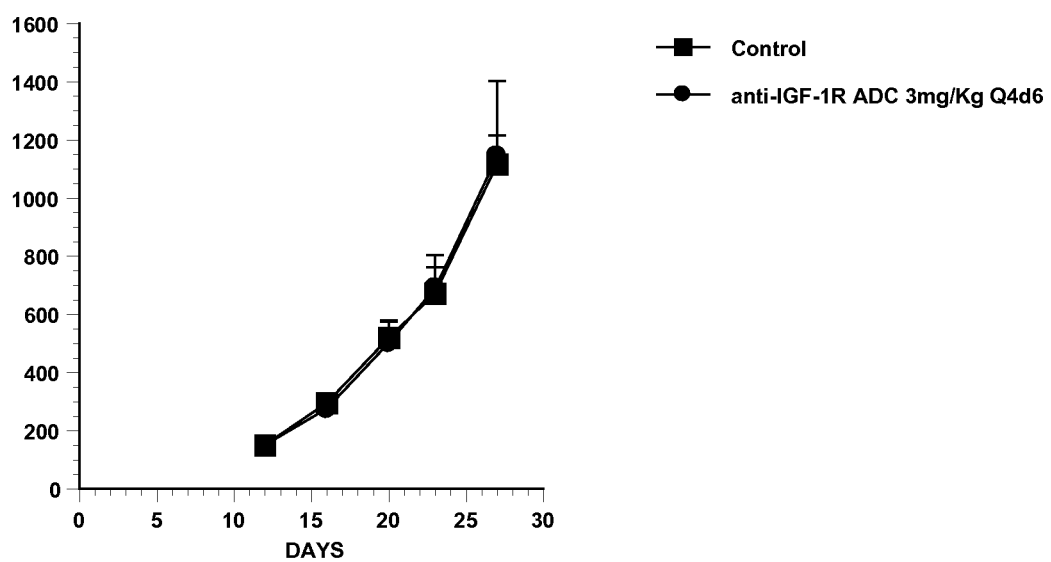

FIG. 5: In vivo activity of an anti-IGF-1R ADC in the SBC-5 xenograft model.

EXAMPLE 1: 816C12 GENERATION AND SELECTION

Mabs generated against IGF-1R were produced and selected as described bellow.

Female Balb/C mice were immunized by subcutaneous injection with 10 µg of recombinant human IGF-1R protein (R and D Systems, 391-GR) with Freund Adjuvant. Immunisation was repeated three times at 2 weeks intervals. The fourth injection was made by intraperitoneal injection in presence of adjuvant.

Three days later spleen cells were fused with SP20Ag14 myeloma cells with PEG 50%. After 14 days of HAT metabolic selection, hybridoma supernatants were tested by FACS using human MCF7 breast cancer cells. Only MCF7 binding antibodies were kept.

Antibodies of interest were then cloned by limit dilution. Eight days after cloning, supernatants were selected once again by FACS using MCF7 cells. Three positive clones were kept. Isotyping of the secreted antibodies is determined using SBA clonotyping system-HRP kit from Southern Biotechnologies (Cat: 5300-05). Finally, one clone is expanded and frozen.

Further characterizations of the 816C12 antibody were then performed using hybridoma supernatant such as rhIGF-1R or rmIGF-1R or rhIR ELISA. In all direct ELISAs, proteins of interest were immobilized (1 µg/ml) to the bottom of each well. After saturation, hybridoma supernatants were added to the wells. After a 1-hour incubation period and a washing step, a solution of goat anti-mouse IgG-HRP labelled polyclonal antibody was used for detection, prior to the addition of the TMB substrate. The reaction was stopped with a 1M $H_2SO_4$ solution before reading the OD with a spectrophotometer at a 450 nm wavelength. Data are presented in Table 6.

TABLE 6

| | OD values obtained at 5 µg/ml by ELISA | | |
|---|---|---|---|
| | rhIGF-1R coating | rmIGF-1R coating | rhIR coating |
| 810D12 | 2.622 | 0.065 | 0.055 |
| Positive CTRL | 2.338 | 1.293 | 1.077 |
| Negative CTRL | 0.055 | 0.065 | 0.048 |

The dose response curve for the 816C12 antibody on rhIGF-1R coating is presented in FIG. 1. The values of the $EC_{50}$ are determined using Prism application.

Data showed that the 816C12 antibody only recognizes the rh IGF-1R with an $EC_{50}$ of 0.41 nM. It does not bind to the murine form of the IGF-1R nor the human IR.

EXAMPLE 2: EVALUATION OF THE CORRELATION OF THE STAGING WITH THE ANTIBODY OF THE INVENTION AND THE ACTIVITY OF AN ADC TARGETING IGF-1R IN THE MCF-7 XENOGRAFT MODEL

In order to correlate the grading of tumors with the pharmacology, the tumors have been graded (section 2.1) and then in vivo experiments on MCF-7 xenograft model have been made with an ADC comprising an antibody moiety targeting the IGF-1R known to be internalized and a drug moiety consisting of an auristatin (section 2.2).

2.1: Immunohistochemistry Detection of the IGF-1R Expression on the MCF-7 Xenograft Model.

Sections of tissue from MCF-7 xenograft were deparaffinized, rehydrated, and placed in Target Retrieval Buffer 1× (Dako S1699) in a boiling bath pre-warm at 98° C. for heat-induced epitope retrieval at 98° C. for 40 minutes then 20 additional minutes in the Target Retrieval Buffer. After 3 washes in Tris Buffer Saline-0.05% tween 20 (TBS-T) (Dako S3006) the Endogenous peroxidase activity was blocked using Peroxidase Blocking Reagent (Dako K4007) for five minutes. Sections were washed with TBS-T and incubated a blocking reagent (UltraV block-TA-125UB-LabVision) for 5 minutes before incubation with either the 816C12 monoclonal antibody (at 5 µg/ml) or mouse IgG1/kappa (5 µg/ml, X0931, Dako) as negative control for 1 hours at room temperature. Sections were washed with TBS-T and incubated with Envision (Dako) for 30 minutes. Diaminobenzidine was used for development of a brown reaction product (Dako K3468). The slides were immersed in hematoxylin for 2 minutes to counterstain (Dako S3309).

Anti-IGF-1R monoclonal antibody 816C12 of the present invention differentially stains the cell membrane of MCF-7. In this IHC procedure, the brown reaction product correlates to positive staining of the cell membrane and lack of brown reaction product correlates to negative staining and no visualization of the cell membrane. Using membranous algorithm, the scoring for the staining of MCF-7 tumor cells was 3+ (FIG. 2A). Using G11 antibody (Roche Ventana) or AF-305 (R&D system) anti-IGF-1R antibodies, section of the same tumor were scored 2+ (FIGS. 2B and 2C respectively).

2.2: In Vivo Activity of an Anti-IGF-1R ADC in the MCF-7 Xenograft Model.

Anti-IGF-1R ADC has been evaluated in vivo, in the MCF-7 xenograft model.

All animal procedures were performed according to the guidelines of the 2010/63/UE Directive on the protection of animals used for scientific purposes. The protocol was approved by the Animal Ethical Committee of the Pierre Fabre Institute. Five millions MCF-7 cells were injected subcutaneous into 7 weeks old Swiss/Nude mice. Prior to cell injection, oestrogen pellets (Innovative Research of America) were implanted to the left flank to mice in order to release estrogens necessary to the in vivo growth of MCF-7 tumors.

Twenty days after MCF-7 cell implantation, when tumors reached an average size of 120-150 mm³, the animals were divided into groups of 6 mice according to tumor size and aspect. Anti-IGF-1R ADC was inoculated by intraperitoneal injections for a 6 injection cycle every four days (Q4d4). The health status of animals was monitored daily. Tumor volume was measured twice a week with an electronic calliper until study end. Tumor volume is calculated with the following formula: $\pi/6 \times length \times width \times height$. Toxicity was evaluated following the weight of animals three times per week. Statistical analyses were performed at each measure using a Mann-Whitney test.

Injection of anti-IGF-1R ADC significantly inhibited and even induced a complete tumor growth regression (FIG. 3) as expected for a tumor graded 3+ but not for a tumor graded 2+.

EXAMPLE 3: EVALUATION OF THE CORRELATION OF THE STAGING WITH THE ANTIBODY OF THE INVENTION AND THE ACTIVITY OF AN ADC TARGETING IGF-1R IN THE SBC-5 XENOGRAFT MODEL

In order to correlate the grading of tumors with the pharmacology, the tumors have been graded (section 3.1) and then in vivo experiments on SBC-5 xenograft model have been made with an ADC comprising an antibody moiety targeting the IGF-1R and a drug moiety consisting of an auristatin (section 3.2).

3.1 Immunohistochemistry Detection of the IGF-1R Expression on the SBC-5 Xenograft Model.

Level of IGF-1R was analyzed using the same protocol described in section 2.1 of the example 2 before.

When IGF-1R was detected with the 816C12, low levels were detected (1+). (FIG. 4A). When IGF-1R was detected with G11 antibody (Roche Ventana) or AF-305 (R&Dsystem) anti-IGF-1R antibodies, sections from the same tumor were scored 3+ (FIGS. 4B and 4C respectively).

3.2: In Viva Activity of an Anti-IGF-1R ADC in the SBC-5 Xenograft Model.

Anti-IGF-1R ADC has been evaluated in vivo, in the SBC-5 xenograft model.

All animal procedures were performed according to the guidelines of the 2010/63/UE Directive on the protection of animals used for scientific purposes. The protocol was approved by the Animal Ethical Committee of the Pierre Fabre Institute. Five millions SBC-5 cells were injected subcutaneous into 7 weeks old Athymic mice. Twelve days after cell implantation, when tumors reached an average size of 150 mm³, the animals were divided into groups of 6 mice according to tumor size and aspect. Anti-IGF-1R ADC was inoculated by intraperitoneal injections for a 6 injection cycle every four days (Q4d6). The health status of animals was monitored daily. Tumor volume was measured twice a week with an electronic calliper until study end. Tumor volume is calculated with the following formula: $\pi/6 \times length \times width \times height$. Toxicity was evaluated following the weight of animals three times per week. Statistical analyses were performed at each measure using a Mann-Whitney test.

Tumor progression of SBC-5 tumoral cells was not affected by injection of anti-IGF-1R ADC. (FIG. 5) as expected for a tumor graded 1+ but not for a tumor graded 3+.

The invention claimed is:

1. An IGF-1R antibody, or an antigen-binding fragment thereof, said antibody comprising:
   i) a heavy chain comprising the following three CDRs, respectively CDR-H1 of sequence SEQ ID No. 1, CDR-H2 of sequence SEQ ID No. 2 and CDR-H3 of sequence SEQ ID No. 3; and
   ii) a light chain comprising the following three CDRs, respectively CDR-L1 of sequence SEQ ID No. 4, CDR-L2 of sequence SEQ ID No. 5 and CDR-L3 of sequence SEQ ID No. 6.

2. The IGF-1R antibody according to claim 1, said antibody comprising a heavy chain variable domain of sequence SEQ ID No. 7, or any sequence with at least 90% of homology with the sequence SEQ ID No. 7; and/or a light chain variable domain of sequence SEQ ID No. 8, or any sequence with at least 90% of homology with the sequence SEQ ID No. 8.

3. An IGF-1R antibody, or an antigen-binding fragment thereof, secreted by the hybridoma deposited at the CNCM, Institut Pasteur, Paris, on Sep. 17, 2014, under number I-4894.

4. A kit for the detection of IGF-1R expressing tumoral cells in a patient, said kit comprising an IGF-1R antibody, or an antigen-binding fragment thereof, said antibody comprising:
   i) a heavy chain comprising the following three CDRs, respectively CDR-H1 of sequence SEQ ID No. 1, CDR-H2 of sequence SEQ ID No. 2 and CDR-H3 of sequence SEQ ID No. 3; and
   ii) a light chain comprising the following three CDRs, respectively CDR-L1 of sequence SEQ ID No. 4, CDR-L2 of sequence SEQ ID No. 5 and CDR-L3 of sequence SEQ ID No. 6; and
   said antibody or antigen-binding thereof being labelled with a detectable moiety.

5. The kit of claim 4, wherein said detectable moiety is selected from the group consisting of fluorophores, chromophores, radionuclides, biotin, and enzymes.

* * * * *